United States Patent [19]

Kirollos et al.

[11] Patent Number: 5,468,645

[45] Date of Patent: Nov. 21, 1995

[54] METHOD FOR REAL-TIME COLORIMETRIC MEASUREMENT OF EXPOSURE TO AIRBORNE POLLUTANTS

[76] Inventors: Kirollos S. Kirollos, 1502 Canterford Ct., Virginia Beach, Va. 23464; Gueorgui M. Mihaylov, 900 E. Piney Branch Dr., Virigina Beach, Va. 23451; Kevin L. Lockerby, 1017 Woodsmans Reach, Chesapeake, Va. 23320; Roman A. Stobnicki, 48 Nestor St., Franklin, N.J. 07416

[21] Appl. No.: 97,112

[22] Filed: Jul. 26, 1993

[51] Int. Cl.⁶ .......................... G01N 21/78; G01N 31/22
[52] U.S. Cl. .......................... 436/164; 436/165; 436/170; 436/805; 436/902; 422/56; 422/58; 422/60; 422/86
[58] Field of Search ................... 422/86, 87, 88, 422/93, 55–58, 59, 60; 436/805, 165, 170, 164, 902; 435/805, 807

[56] References Cited

U.S. PATENT DOCUMENTS

| | | | |
|---|---|---|---|
| Re. 31,879 | 5/1985 | Lubbers et al. | 436/133 |
| 3,985,017 | 10/1976 | Goldsmith | 73/23 |
| 4,269,804 | 5/1981 | Kring | 422/86 |
| 4,271,121 | 6/1981 | Diller | 422/56 |
| 4,421,719 | 12/1983 | Burleigh | 422/57 |
| 4,459,266 | 7/1984 | Lamoreaux | 422/86 |
| 4,478,792 | 10/1984 | McConnaughey et al. | 422/58 |
| 4,748,930 | 6/1988 | Leichnitz | 116/206 |
| 4,863,694 | 9/1989 | Kimmel et al. | 422/86 |
| 4,948,975 | 8/1990 | Erwin et al. | 250/361 C |
| 5,055,267 | 10/1991 | Buwoughs et al. | 422/83 |
| 5,075,544 | 12/1991 | Sato et al. | 250/226 |
| 5,089,232 | 2/1992 | May | 422/83 |
| 5,091,154 | 2/1992 | Pauli et al. | 422/63 |
| 5,120,507 | 6/1992 | Sano et al. | 422/82.05 |
| 5,246,858 | 9/1993 | Arbuckle et al. | 436/8 |
| 5,298,741 | 3/1994 | Walt et al. | 250/227.23 |

*Primary Examiner*—James C. Housel
*Assistant Examiner*—Harold Y. Pyon
*Attorney, Agent, or Firm*—E. Lieberstein

[57] ABSTRACT

A method for reading and analyzing a diffusion-cell colorimetric exposimeter for making a quantitative determination of the time-weighted average (TWA) exposure to airborne gases or vapors. The diffusion cell is optically scanned to form color video signal data representative of the primary color components of the image formed from the reaction of the chromophoric reagent and pollutant. The data is converted to digital data and processed to compute exposure for a given pollutant gas as a function of color intensity for at least one of the primary color components.

9 Claims, 5 Drawing Sheets

METHOD FOR REAL-TIME COLORIMETRIC MEASUREMENT OF EXPOSURE TO AIRBORNE POLLUTANTS

FIELD OF THE INVENTION

This invention relates to a method for reading a diffusion-cell, colorimetric exposimeter, to provide a quantitative determination of the time-weighted, average (TWA) exposure to airborne, organic gases or vapors.

BACKGROUND OF THE INVENTION

Time-weighted, average (TWA) exposure measurements to toxic gases and vapors in the atmosphere is necessary to insure compliance with government occupational hygiene standards. One method to accomplish this involves drawing an air sample through a tube containing a sorbent, and analyzing the sorbent, usually by gas chromatography, to make a quantitative determination of the sorbed, organic compounds. This technique is time-consuming, labor-intensive, and costly. More recently, colorimetric sampling devices have been developed, referred to in the art as "dosimeters" or "exposimeters," which are made available in the form of a badge, to be worn on the lapel of a worker, or mounted in a specific location, for a fixed time period, to enable a real-time measurement to be made of the exposure level of a gas or vapor pollutant in the atmosphere. Such devices are passive and depend on gas permeation and diffusion through the device to provide a real-time measurement of the exposure level to a pollutant gas. The measurement may be either a visual indication of the relative exposure level or a comparative measurement. Heretofore, a real-time, quantitative measurement of the time-weighted average exposure (TWA) was not available.

Several methods are known for estimating the time-weighted average (TWA) exposure and short-term exposure limit (STEL) to toxic gases and vapors in the atmosphere. These methods may be classified into the following major categories:

1. Methods which use the quality of a received colorimetric result (density, color, tone, shade, keen, or nuance), for comparison with a given color standard. The colorimetric devices in this category rely on the pollutant reacting chemically with reagent(s) dispersed on a suitable support to produce a color change. The estimation of pollutant is semi-quantitative, and it is reliable only in a comparably narrow exposure interval.

2. Methods which use the quantity of the received color expressed by area or length of stain. In general, the devices in this category consist of transparent tubes filled with a granular solid support impregnated with colorimetric reagent(s). Pollutants penetrate by diffusion through a diffusion retainer into the tubes and react with the colorimetric reagent(s). A colorimetric result forms as a length of stain proportional to the total exposure value of the concentration multiplied by the exposure time, that is, CT value. This provides a simple visual measure of exposure by comparing the length of stain to a fixed scale. However, the colorimetric result is nonlinear, and the response time changes with the length of stain.

3. Methods which rely upon the degree of gas permeation and/or gas diffusion to control the degree of gas penetration through a chromophoric reagent(s) to determine dosage exposure. These devices are referred to as "direct-read" because they visually provide a graded sensitivity of color detection for real-time measurement. One example of a direct-read, colorimetric dosimeter is taught in U.S. Pat. No. 4,478,792, in which a stack of porous sheets are impregnated with a reagent, causing the sheets in the stack to sequentially change color upon exposure to a gas pollutant in proportion to the degree of gas penetration. The degree of gas penetration is a function of the gas concentration in the atmosphere over a given time period. Another direct-read, colorimetric dosimeter is taught in U.S. Pat. No. 4,271,121, in which the indicator layer containing the colorimetric reagent is subdivided into a plurality of measuring fields. A graded sensitivity in color detection is achieved using a plurality of membranes of filter paper superimposed over the indicator layer in a staggered relationship, or by using different membrane thicknesses. The variation in membrane thickness or the staggered membrane arrangement varies with the diffusion resistance to the separate measuring fields in the indicator layer and, accordingly, varies the degree of gas penetration to each measuring field.

A more practical and useful direct-read, colorimetric exposimeter is taught in copending patent application entitled "Direct Read Colorimetric Exposimeter," Ser. No. 07/969,762, filed Oct. 30, 1992, now abandoned and assigned to the common assignee of the subject application. In this application, the disclosure of which is herein incorporated by reference, graded sensitivity to color detection is achieved by forming multiple measuring zones or fields, with each such zone or field hereinafter defined as a "diffusion cell." The exposimeter thus contains multiple diffusion cells, with each diffusion cell composed of a color indicator containing a chromophoric reagent which changes color when exposed to the polluting gas or vapor to be measured, and at least one gas-diffusion control member which provides a predetermined diffusion resistance to said polluting gas or vapor. Accordingly, each diffusion cell has a defined sensitivity to said pollutant and forms, in combination with the other diffusion cells in the exposimeter, an expanded dosage range for providing a graded measurement of color variation to most polluting gases.

The present invention is directed to a method and device for reading and analyzing a diffusion-cell, colorimetric exposimeter for making a quantitative determination of the time-weighted average (TWA) exposure to airborne gases or vapors.

SUMMARY OF THE INVENTION

In accordance with the method of the present invention, a diffusion-cell, colorimetric exposimeter is exposed to a test atmosphere for analyzing and measuring the concentration of a pollutant gas or vapor, in which the diffusion cell in said exposimeter contains a chromophoric reagent responsive to a given pollutant gas or vapor, and a diffusion control means for providing the cell with a specified diffusion resistance to said pollutant gas or vapor, said method comprising the steps of:

(a) optically scanning said cell at a selected resolution to form electrical color video signal data representative of the primary color components of the color image formed in such cell from the reaction of the chromophoric reagent and pollutant, with the magnitude of the signal data equal to the color intensity;

(b) converting said color video data into corresponding digital data; and (c) processing said digital data to compute the exposure dosage for a given pollutant gas or vapor as a function of color intensity for at least one of said primary color components.

The present invention is also directed to a device for reading and analyzing a diffusion-cell, colorimetric exposimeter to provide a quantitative measurement of the level of exposure to a given polluting gas or vapor in the ambient atmosphere, with such cell having a color-forming indicator containing a chromophoric chemical reagent, which changes color when exposed to a polluting gas or vapor, and gas-diffusion control means for providing such cell with a preselected diffusion resistance to said polluting gas or vapor, comprising:

means for optically scanning said cell at a selected resolution to form electrical color video signal data representative of the primary colors in such cell, with the magnitude of the signal data corresponding to color intensity;

means for converting said color video data into corresponding digital data;

bar code means for providing information identifying the chromophoric reagent in the exposimeter, defining minimum and maximum exposure dosage, and providing data representative of the coefficients of a given relationship between exposure dosage and color intensity under simulated conditions;

means for optically scanning said bar code for converting the bar code information and data into digital information; and microprocessor means for computing said dosage level, based on said digital information from said bar code, and said digital data for at least one of said primary color components.

BRIEF DESCRIPTION OF THE DRAWINGS

Other advantages of the present invention will become apparent from the following detailed description thereof when read in conjunction with the accompanying drawings, of which.

DETAILED DESCRIPTION OF THE INVENTION

Figure 1:
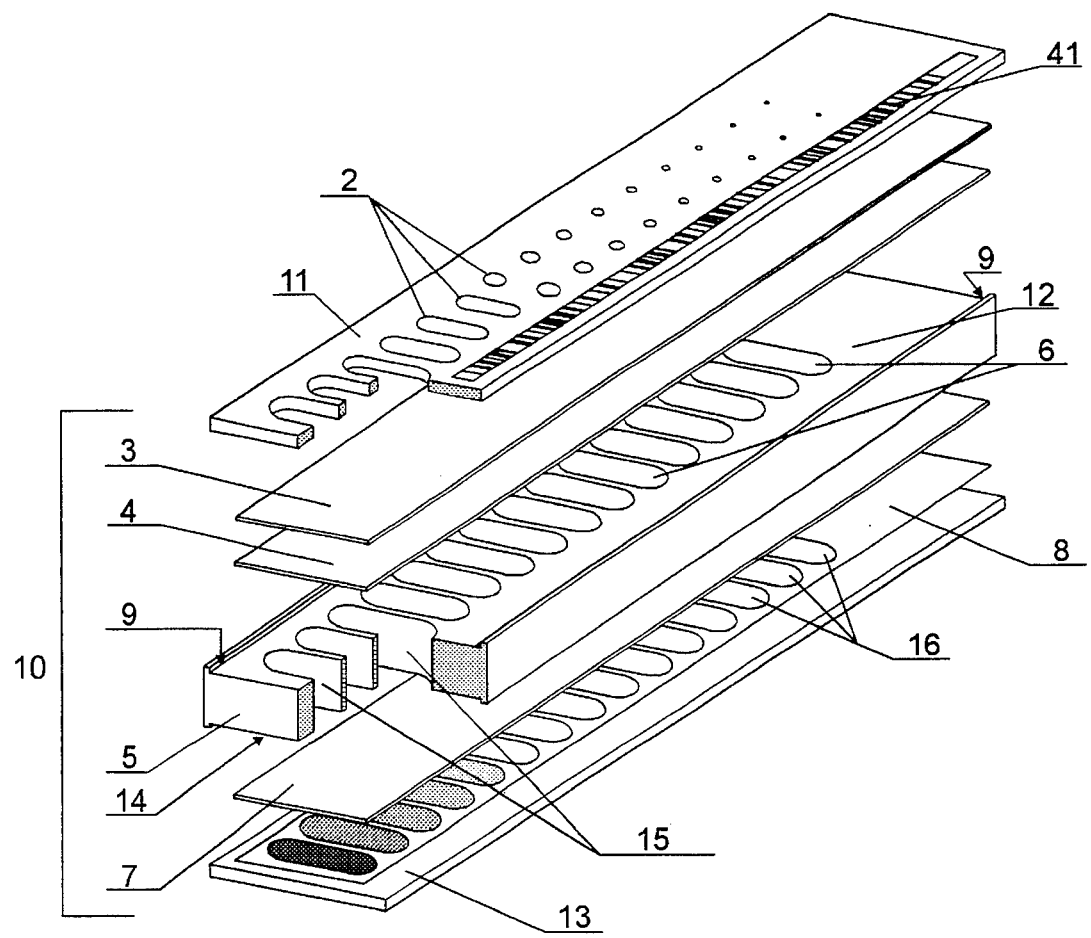
FIG. 1 is an exploded view in perspective of a multiple-cell, colorimetric, gas-diffusive exposimeter, for use in accordance with the present invention.

A direct-read, autogenic, multiple-cell, colorimetric exposimeter (10) is shown in FIG. 1 for passive monitoring of the atmosphere to measure the concentration of a given, preselected gas or vapor pollutant. The exposimeter (10) has a substantially rectangular body (5) composed of a solid gas-impermeable material of, preferably, plastic, with multiple openings (6) extending vertically through the body (5). The multiple openings (6) are arranged in any sequence, which is preferably in linear alignment, for forming a single row. The openings (6) are preferably identical in size and geometry, and extend from the top side (12) of the body (5) to the bottom side (14) thereof. A cover plate (11) is secured to the top side (12) and a bottom plate (13) to the bottom side (14). The bottom plate (13) should be transparent or have transparent windows (17) in vertical alignment with the openings (6). The cover plate (11) has an array of holes (2) in a predetermined arrangement relative to the openings (6), to provide a select number of holes for each opening (6). The holes (2) may vary in size or geometry or both, so that the area exposed to the atmosphere through the holes (2) above each opening (6) is predefined.

A diffusive, porous member (3) is interposed between the cover plate (11) and all of the openings (6) on the top side (12) of the body (5) of the exposimeter (10). An additional "trapping" member (4) having a function to trap certain cross-interfering substances or to convert said substances to a more chemically convenient form for trapping, may, if desired, be superimposed over the openings (6) adjacent to the member (3). A color-indicator layer (8) is interposed on the bottom side (14) of the body (5), between the bottom plate (13) and the openings (6). An additional light-contrast diffusion member (7) having a function of optimizing the optical reading process may also, if desired, be interposed between the color-indicator layer (8) and the openings (6) on the bottom side (14). The cover plate (11) and the bottom plate (13) are secured to the body (5) along the edges (9) on the top and bottom sides (12) and (14), respectively.

The color-forming indicator layer (8) may be constructed from any porous material, including paper, plastic, or fabric, impregnated with a chromophoric reagent sensitive to a particular gas or vapor. Alternatively, the reagent chemical can be coated on a substrate carrier medium, with the coating of chemical reagent facing the openings (6) in the body (5). The composition of the reagent is selected based on the polluting gas to be detected. Accordingly, if the polluting gas is $H_2S$, the chemical reagent may be a composition containing, for example, white lead acetate, which as well known to those skilled in the art, will react with $H_2S$ to form black lead sulfide.

Each opening (6) of the exposimeter (10) in combination with the section of indicator layer (8) in alignment therewith defines a "diffusion cell" (15), for purposes of the present invention, with each diffusion cell referred to hereinafter simply as a "cell." Accordingly, the exposimeter (10) of FIG. 1 has seventeen cells (15), one of which is used as a reference cell (16). The size of the holes (2) located in the cover plate (11) above each such cell (15), the dimensions of each opening (6) inclusive of its length, the porosity of the diffusive, porous member (3), and any other membrane, if used, determine the diffusion resistance of the cell (15). The contaminant air permeates through the holes (2) and diffuses through each cell (15) into contact with the indicator layer (8), to form a multiple number of colored images, corresponding to the number of cells. The colored images depend on the chemical reaction between the indicator layer (8) and the gas or vapor contaminant. The progression of color between the cells (15) is determined by the controlled progression of diffusion resistance between the cells (15).

The diffusive, porous member (3) may be composed of a porous material, such as paper, or, if desired, may represent a control diffusion member, as taught in the corresponding patent application, Ser. No. 07/969,762, filed Oct. 30, 1992, which, as earlier mentioned, describes a multiple-cell, colorimetric, gas-diffusive exposimeter, in which the diffusion resistance is controlled by varying the porosity through each control diffusion member. It should be understood that the method and device of the present invention is not limited to any specific multiple-cell construction. In fact, many variations of cell geometry and/or variations in the geometry or size of the holes (2), as well as in the diffusive, porous member (3), may be used to control the permeation and diffusion resistance through each cell (15) of the exposimeter (10).

An airborne pollutant will pass through each cell (15) in the exposimeter (10) in accordance with Fick's First Law of Diffusion as follows:

$$M=1/K(CT) \tag{1}$$

where

M=mass of pollutant transported across the diffusive resistance K

C=mean concentration acting on the device

T=time of exposure

K=total diffusive resistance

On the other hand, $$K=L/AD \tag{2}$$

where

A=cross-sectional area of the diffusion path

L=length of the diffusion path and/or thickness of a porous material used as diffusive resistance D=diffusion coefficient of the diffusing pollutant through the chamber and/or porous material.

The diffusion resistance of each cell (15) controls the concentration of contaminant entering the indicator layer for a given exposure time. The diffusion resistance is readily varied from cell to cell to provide a predetermined progression of color enhancement, which is utilized in accordance with the present invention, as color information from which total dosage may be quantified.

Figure 2:
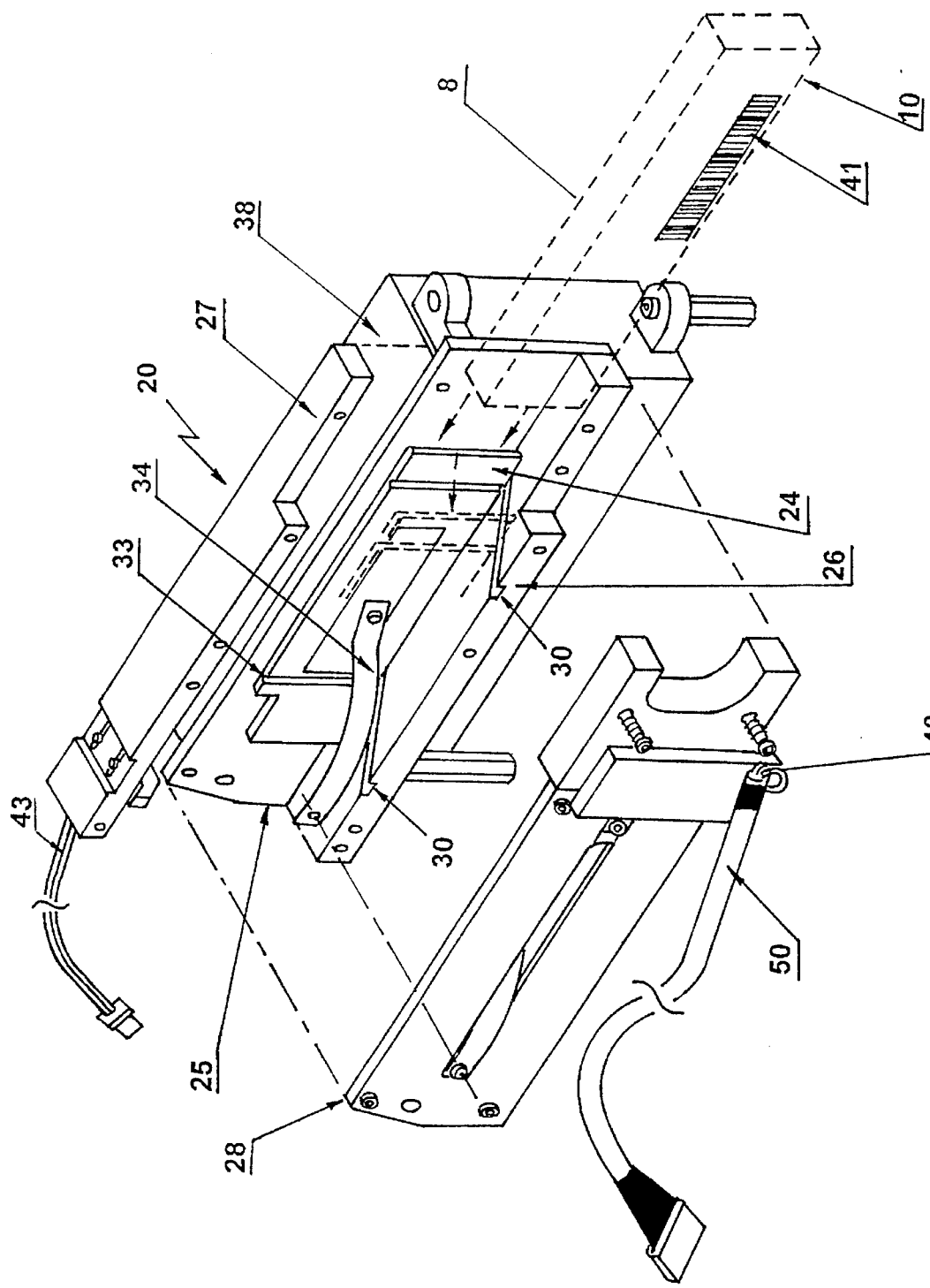
FIG. 2 is a perspective view of the device of the present invention for reading the colorimetric, diffusive gas exposimeter of FIG. 1.

The reading device (20), as shown in FIG. 2, reads the color and color intensity in each cell of the exposimeter and computes the (TWA) exposure for a given polluting gas.

The reading device (20) comprises a housing (22) having a movable shutter (24) mounted on an optically clear plate (25), a pair of support plates (26) and (27) extending from opposing ends of the optically clear plate (25), and a front cover (28) mounted over the support plates (26) and (27), to form an opening between the plate (25) and the front cover (28), for introducing an exposimeter (10), as shown in FIG. 1, which hereinafter will simply be referred to as a "badge." The support plate (26) includes two slots (30) and (31) disposed at an inclined angle relative to the optically clear plate (25). Corresponding slots (not shown) are formed in the support plate (27). A pair of dowels (32) and (33) extend from opposite sides of the shutter (24) into the slots (30) and (31) of each of the support plates (26) and (27). This permits the shutter (24) to move along the slots in each wall in response to the force of the badge (10) as it is pushed into the device (20). A compression spring (34) is positioned between the shutter (24) and the front cover (28) to urge the shutter (24) toward the plate (25), so that the shutter (24) normally rests on the optically clear plate (25), except when displaced by the badge (10). The reading device (20) also contains an optical scanning head (38), which is supported by the support plates (26) and (27), to scan the color image produced on the indicator layer (8) corresponding to each cell (15) of the exposimeter (10). A bar code scanning head (40) is mounted on the front cover (28) and is aligned to read the bar code label (41) which is affixed to the badge (10). The bar code label (41) contains data which identifies the chromophoric reagent chemistry and additional information necessary to evaluate and measure the color read from the badge, as will be more fully explained hereafter.

Figure 3:
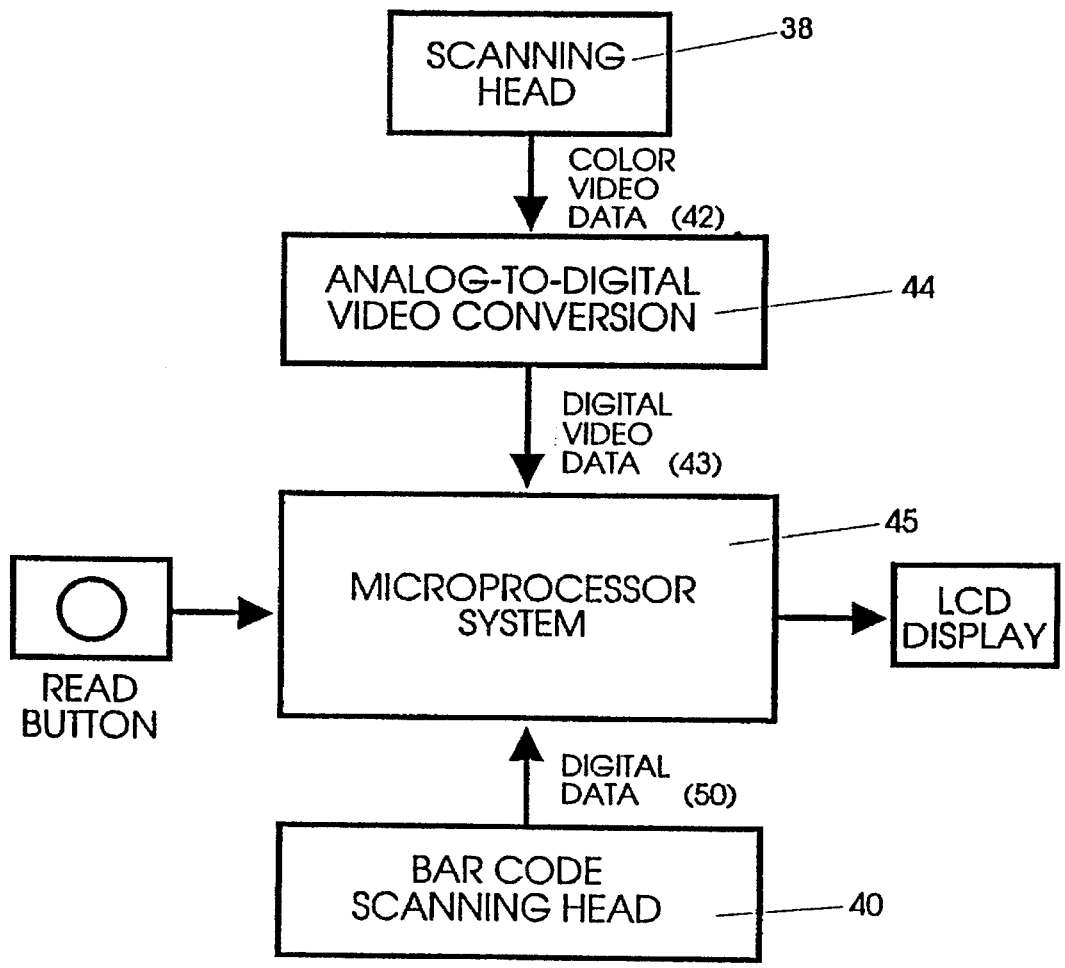
FIG. 3 is a schematic block diagram of the computing system in the;device shown in FIG. 2.
Figure 4:
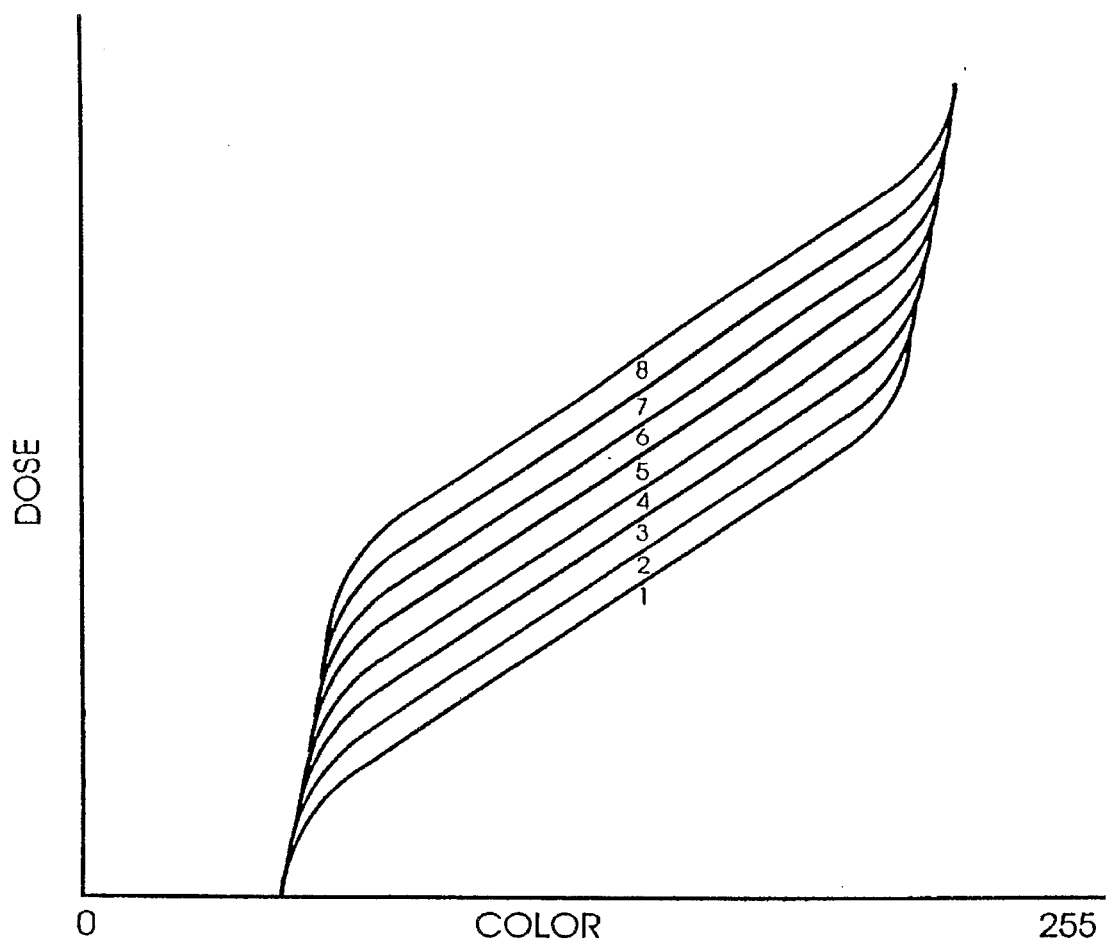
FIG. 4 is a graph illustrating the relationship between dose and color intensity for some of the cells in the device of FIG. 1.
Figure 5:
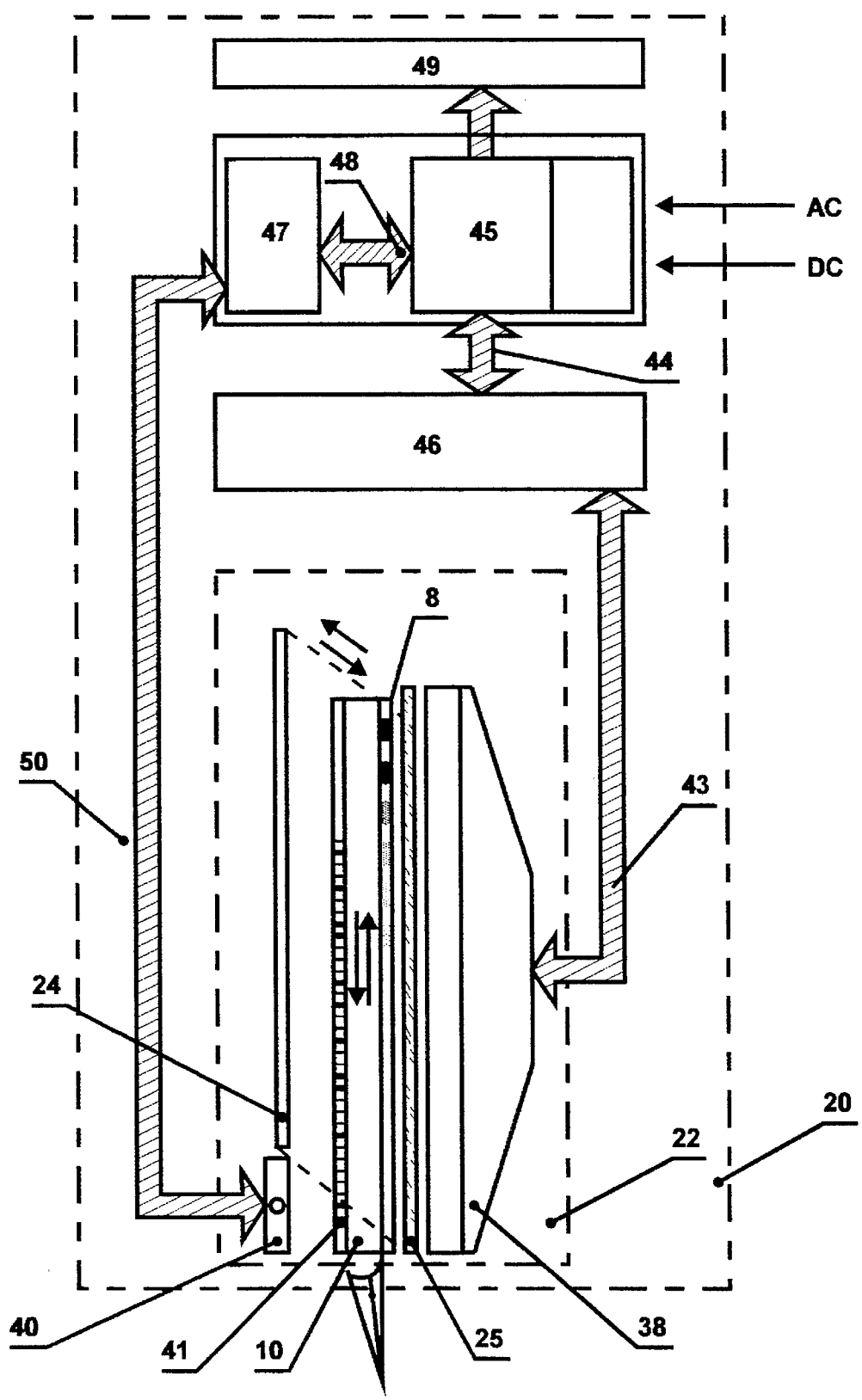
FIG. 5 is a schematic drawing, partially in block diagram form and partially diagrammatic, showing the integration of the reader and exposimeter in accordance with the present invention.

The operation of the reading device (20) is best understood in connection with the schematic block diagram of FIG. 3, in conjunction with the graph of FIG. 4 and the schematic drawing of FIG. 5.

The optical scanning head (38) is a conventional, commercially available device which includes a source of illumination of preferably white light in the visible wavelength region of the electromagnetic spectrum, and a conventional, charge-coupled scanning device composed of micro-cells which is analogous to an array of photodiodes arranged to discriminate between the wavelengths of light reflected from the target, i.e., the indicator layer (8) for forming electrical video signal data (42) representative of each of the primary color components—viz., red, blue, and green—of the color image formed over the entire length of the indicator layer (8). The electrical video signal data (42) corresponds to the intensity of the image for each of the primary colors, and is converted to digital data (43) by an analog to digital converter (44), preferably forming an eight-digit decimal number, corresponding to each pixel of information for each color component—red, blue, and green. Accordingly, each eight-digit decimal number may have any value within the range of 0–255 ($2^8-1$). With the badge fully inserted into the reading device (20), the scanning head (38) is aligned in juxtaposition with the openings (6) of the badge (10), and can scan the indicator layer (8), either in sequence or simultaneously. It is preferred to scan all of the cells in the badge (10) simultaneously. The resolution of the optical scanning head (38) is fixed by the manufacturer. The optical scanning head (38) selected for use in the reader (20) has a fixed resolution of two hundred dots per inch (200 dpi) and is four inches long. Accordingly, the scanning head (38) reads the three color lines for a total of 800 pixels for each color component, or 2,400 pixels for all color components, assuming all of the cells are read. The number of cells to be read is determined from an evaluation of the data received from the badge (10), based on the chromophoric reagent chemistry.

For the color information read by the scanning head (38) to be meaningful, the reader (20) must be calibrated against a white-and-black background. The optically clear plate (25) has a flat sheet (46) of white-colored material, such as white paper, mounted on the shutter (24). Before the badge (10) is inserted into the reader (20), the reader is calibrated by a calibration sequence involving turning off the source of illumination in the optical scanning head (38) to obtain a data value corresponding to the color "black," followed by turning on the source of illumination in the optical scanning head to obtain a data value corresponding to 100% "white" light. This calibration sequence may be continuously repeated until the badge (10) is inserted. A "black" and "white" threshold value is preferably obtained for each primary color component. The optical scanning head (38) then reads the color image formed on the indicator layer in comparison to the threshold "black" and "white" values so that the electrical signal data (42) is consistent for each reading and to assure consistent readings.

The digital data (43) is fed into a microprocessor (45) which is programmed to compute the dosage level of the polluting gas from the data (43) and from digital data (50) received from the bar code scanning head (40). The digital data (50) corresponds to the information on the bar code label (41).

The color formed in each cell of the exposimeter (10) is proportional to the exposure value of the concentration of pollutant in each cell multiplied by exposure time, i.e., the CT value identified in equation (1) of Fick's First Law of Diffusion. The relationship between exposure, hereafter referred to as "dose" and color intensity, is illustrated in FIG. 4 for the first eight cells, with the understanding that the remaining eight cells, exclusive of the reference cell, will exhibit the same dose-versus-color intensity relationship as the first eight cells, following a similar progression displaced above the first set of curves.

As previously mentioned, the intensity of the color developed is proportional to the exposure dose (CT value). To compute exposure dosage, a relationship is first established between color information, as converted into digital data, and exposure dosage under simulated atmospheric conditions for a specific pollutant and a specific reagent.

The badge is removed from the simulated atmosphere in specific intervals and inserted in the reader to obtain digital values corresponding to the colors developed in the badge at that specific concentration for different exposure times, that is, having different digital values corresponding to different exposure doses for different CT values. Having a set of digital values corresponding to a set of CT values, any conventional mathematical means may be used to define at least one logarithmic, linear, second- or third-order relationship between the digital values and exposure doses. The coefficients of these curves are decoded in the bar code. Thus, by exposing sample badges to known concentrations of contaminant gases in laboratory conditions, a desired linear or nonlinear relationship can be established which relates the color to the exposure dose.

The exposure dose may be mathematically related to color as follows:

$$D = \chi f(C)$$

where

D corresponds to dosage level for any given chromophoric reagent,

C corresponds to the color intensity for at least one primary color, and

X is a color intensity coefficient for a given chromophoric reagent chemistry.

The model algorithm used to compute exposure dose from the color data values can be formulated in several ways, such as, for example: 1) average all pixel data points for an individual color in each cell, 2) integrating all of the pixel data points for a particular color for each cell, 3) averaging all of the pixel data points for two or more colors, etc.

Since the total color is proportional to the exposure dose, the sum of the array for one particular color should increase respectively for monitors which are exposed to a higher dose.

The equation selected to satisfy the functional relationship $D = \chi f(C)$ can be expressed as a polynomial, a logarithmic, or a more complex equation. The general equation for each curve of FIG. 4 in the linear region is polynomial and may be expressed as $y = mx + b$, where y equals the CT value, x equals color intensity, and m and b are coefficients which are derived by linear or nonlinear regression. The total color formed in all of the cells is derived by integrating the area under the curve. A basic form of mathematical expression which defines a preferred model relationship to compute dosage from total color is as follows:

$$\log D = A + B \log C$$

where

D = dose;

C corresponds to the color intensity for at least one primary color component; and A, B are predetermined coefficients which may be derived by linear or nonlinear regression techniques, as is known to those skilled in the art, to yield minimum error.

Linear and nonlinear multiple regression techniques are well-known and many computer programs are conventionally available to perform regression analysis.

It should be understood that the above calculation of dosage is based on the total color of at least one of the primary color components detected in each cell. The determination of which one or more of the primary colors—red, blue, or green—is to be used is based on the reagent chemistry used in the badge (10). This information is identified in advance and incorporated in the bar code label (41). The coefficients A and B are also identified in advance for a given reagent chemistry, and are based on simulated testing and/or regression estimation, as explained earlier.

It should further be understood that any curve-fitting algorithm can be used to define a linear or nonlinear relationship to correlate exposure dosage for one or more the primary colors. The relationship of exposure dosage to each primary color is mutually exclusive. One or more color components can be arbitrarily chosen for the calibration equation. Each badge has a specific chemical reaction dependent upon the compound which is to be detected. Furthermore, the color developed is specific to that chemical reaction. For this reason, some badges will have a more accurate correlation with one color over another, for example, a chlorine badge will have a better correlation coefficient for green over blue and red. Sulfur dioxide may have a better correlation coefficient from the red component, etc.

The microprocessor may be programmed to evaluate the scanned data (43) to detect which of the higher number cells have saturated based on their color intensity value, and which of the lower number cells have insufficient color intensity, i.e., little or no color. The information of the remaining cells will then be used to compute the value "C" in the selected model relationship.

Alternatively, the data from the cells can be evaluated to determine the degree of sensitivity required of the cells for the pollutant under examination. In this instance, two or more model equations can be used equivalent in form to any of the expressions identified above, with the coefficients predetermined for each equation, thereby forming a plurality of sensitivity ranges. A determination of which equation is used may be based on analysis of the scanning data (43), so that the microprocessor will automatically use the appropriate equation based on desired sensitivity for the reagent chemistry and pollutant under examination. The determination of a plurality of model equations may also be directed from the bar code label (41), and, as such, ties the method of dosage analysis to the reagent chemistry of the specific badge (10). The bar code label (41) is specific to a badge (10) for a specific reagent chemistry.

Many variations are readily foreseeable for processing the color information, either individually from each cell with the aggregate summed up and arranged to provide total dosage, or by processing the color information from all of the cells in the aggregate as one expanded range.

As explained earlier, at least one of the seventeen (17) cells (15) in the badge (10) is used as a reference cell (16), preferably the last cell, although any cell may be used as a reference cell. The function of the reference cell (16) is to serve as an indicator that the badge (10) is unusable, i.e., it is defective. The reference cell (16) is of itself identical in all respects to all of the other cells (15) in the badge (10). However, no hole (2) exists in the cover plate (11) above the reference cell (16) and, as such, the reference cell (16) is not exposed to the atmosphere. Accordingly, the reference cell (16) should not cause any chemical reaction to occur in the indicator layer (8) aligned with the reference cell (16), unless the badge (10) is exposed to a temperature variation or as a result of age or a combination sets off a chemical reaction forming a color. The microprocessor (45) may be programmed to respond to a detection of color in the reference cell (16) above a threshold, and form a signal indicative of this situation or to override any computation for this badge (10) other than to indicate a defect.

What is claimed is:

1. A method for providing a quantitative determination of the concentration of a preselected pollutant gas or vapor in the atmosphere comprising the steps of:

(a) forming a series arrangement of gas diffusion cells with each cell having a chromophoric reagent chemical responsive to said pollutant gas or vapor, and each cell being exposed to the atmosphere having a different diffusion resistance means to provide a predetermined diffusion resistance to said pollutant gas or vapor and with the arrangement providing a constant diffusion pathlength through each cell such that said gas diffusion cells all respond in coincidence to the concentration of said pollutant gas in the atmosphere and in a relationship corresponding to the arrangement of said cells whereby the exposure of each cell to said pollutant gas or vapor can be sampled with a constant response time independent of the concentration of the gas and the sampling time;

(b) illuminating each of said cells with light from a light source;

(c) optically scanning reflected light from said cells to form color video signal data representative of the primary color components of the color image formed in the cell from the reaction of the chromophoric reagent and pollutant, with the magnitude of the signal data corresponding to the color intensity;

(d) converting said color video data into corresponding digital data for at least one primary color component of the reflected light;

(e) feeding said digital data into a microprocessor programmed to automatically compute a quantitative value of exposure dosage for said given pollutant gas or vapor in the atmosphere as a function of said digital data for at least said one primary color component in accordance with the following mathematical relationship:

$D=\chi f(C)$ where

D corresponds to the exposure dosage;

C corresponds to said digital data and $\chi$ equals a predetermined color intensity coefficient corresponding to said given pollutant gas or vapor and (f) displaying the computed exposure dosage as a quantitative value.

2. A method, as defined in claim 1, wherein the digital data is processed using a model relationship to compute dosage from total color as follows:

$$\log D = A + B \log C$$

where

D=dose;

C corresponds to the color intensity for one primary color component; and

A, B are predetermined coefficients.

3. A method, as defined in claim 1 wherein a reference cell is provided in addition to said arrangement, said reference cell being isolated from the atmosphere and providing a reference reading.

4. A method, as defined in claim 3, wherein said cells are serially arranged relative to one another.

5. A method, as defined in claim 4, wherein said digital data is processed from the cells.

6. A method, as defined in claim 4, wherein said digital data is processed from a selected number of such cells.

7. A method, as defined in claim 5, wherein said digital data is processed by a microprocessor programmed to evaluate said data to detect which of said cells should be used to compute the value "C" in said algorithm.

8. A method, as defined in claim 7, wherein said multiple number of gas diffusion cells are calibrated to read color against a background corresponding to 100% white light and to the absence of light, i.e., to black.

9. A method, as defined in claim 7, further comprising more than one model relationship for computing dosage, and selecting the model relationship based on the evaluation of said data.

* * * * *